(12) United States Patent
Petitte et al.

(10) Patent No.: US 6,333,192 B1
(45) Date of Patent: Dec. 25, 2001

(54) METHOD OF PRODUCING AN UNDIFFERENTIATED AVIAN CELL CULTURE USING AVIAN PRIMORDIAL GERM CELLS

(75) Inventors: James N. Petitte; Il-Kuk Chang, both of Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/370,708

(22) Filed: Aug. 9, 1999

(51) Int. Cl.$^7$ ........................................................ L12N 5/00
(52) U.S. Cl. .................... 435/349; 435/325; 435/347; 435/373; 435/377
(58) Field of Search ................................ 435/325, 373, 435/377, 349, 347

(56) References Cited

U.S. PATENT DOCUMENTS

| | | |
|---|---|---|
| 5,166,065 | * 11/1992 | Williams et al. . |
| 5,340,740 | 8/1994 | Petitte et al. . |
| 5,453,357 | 9/1995 | Hogan . |
| 5,656,479 | 8/1997 | Petitte et al. . |
| 5,670,372 | 9/1997 | Hogan . |
| 5,690,926 | 11/1997 | Hogan . |
| 5,830,510 | 11/1998 | Petitte et al. . |
| 5,985,659 | * 11/1999 | Kusakabe et al. . |

FOREIGN PATENT DOCUMENTS

| | | |
|---|---|---|
| WO96/12793 | 5/1996 | (WO) . |
| WO99/06533 | 2/1999 | (WO) . |
| WO99/06534 | 2/1999 | (WO) . |

OTHER PUBLICATIONS

Pettite, J.N., "The Origin of the Avian Germ Line and Transgenesis in Birds," Poultry Science, PSA Excellence in Science Publishing (San Diego), vol. 76 (No. 8), pp. 1084–1092, (Aug. 9, 1997).

Chang, I.K., "Production of Germline Chimeric Chickens By Transfer of Cultured Primordial Germ Cells," Cell Biology International, Seoul National University (Suweon, Korea), vol. 21 (No. 8), pp. 495–499, (Aug. 1997).

Chang, I.K., "Germ Line Chimera Produced By Transfer of Cultured Chick Primordial Germ Cells," Cell Biology International, Institute of Physical and Chemical Research (Tsukuba Science City, Japan), vol. 19 (No 7), pp. 569–576, (Jul. 1995).

* cited by examiner

Primary Examiner—Leon B. Lankford, Jr.
(74) Attorney, Agent, or Firm—Jenkens & Wilson, P.A.

(57) ABSTRACT

A method of producing undifferentiated avian cells expressing an embryonic stem cell phenotype. The method includes the steps of collecting avian gonadal cells comprising primordial germ cells from an avian embryo after the formation of the primitive streak; depositing the avian gonadal cells in contact with a preconditioned feeder matrix; and growing the avian gonadal cells on the pre-conditioned feeder matrix in the presence of media for a time sufficient to produce an avian cell culture consisting essentially of undifferentiated avian cells expressing an embryonic stem cell phenotype.

43 Claims, 5 Drawing Sheets

METHOD OF PRODUCING AN UNDIFFERENTIATED AVIAN CELL CULTURE USING AVIAN PRIMORDIAL GERM CELLS

TECHNICAL FIELD

The present invention relates to undifferentiated avian cells expressing an embryonic stem cell phenotype in general, and particularly relates to avian primordial germ cells and undifferentiated avian cells expressing an embryonic stem cell phenotype.

| Table of Abbreviations | |
|---|---|
| ATCC | American Type Culture Collection |
| bFGF | basic fibroblast growth factor |
| BRL | buffalo rat liver |
| DMEM | Dulbecco's modified Eagle's medium |
| EDTA | ethylenediamine tetraacetate |
| ES | embryonic stem |
| ESCs | embryonic stem cells |
| FBS | fetal bovine serum |
| FGF | fibroblast growth factor |
| H&H | Hanburger & Hamilton staging system |
| IGF | insulin-like growth factor |
| LIF | leukemia inhibitory factor |
| PBS | phosphate buffered saline |
| PGCs | primordial germ cells |
| SSEA-1 | stage-specific mouse embryonic antigen-1 marker for PGCs and ESCs |
| STO | mouse fibroblast cell line |
| SCF | stem cell factor (also called steel factor or SF) |
| TGF-$\beta$1 | transforming growth factor-$\beta$1 |

BACKGROUND ART

In mammals, primordial germ cells cultured from the genital ridge have the ability to give rise to pluripotent embryonic stem cells. For example, U.S. Pat. Nos. 5,690,926 issued Nov. 25, 1997 to Hogan; 5,670,372 issued Sep. 23, 1997 to Hogan; and 5,537,357 issued Sep. 26, 1995 to Hogan each disclose pluripotential mammalian embryonic stem cells and methods of making the same. The disclosure of these patents is limited to mammalian embryonic stem cells and particularly to the culturing of murine and other mammalian embryonic stem cells using a combination of growth factors consisting of SCF, FGF and LIF.

Current prior art reports on the culture of avian primordial germ cells (PGCs) have concentrated on efforts to maintain a PGC-phenotype and to stimulate proliferation. See e.g., Chang, I. K. et al., *Cell. Biol. Int.* 1997 August; 21(8): 495–9; Chang, I. K. et al., *Cell. Biol. Int.* 1995 February; 19(2): 143–9; Allioli, N. et al., *Dev. Biol.* 1994 September; 165(1): 30–7 and PCT Publication No. WO 99/06533, published Feb. 11, 1999 (Applicant—University of Massachusetts; Inventors—Ponce de Leon et al.).

Undifferentiated avian cells expressing an embryonic stem cell (ESC) phenotype and processes for producing the same are disclosed in U.S. Pat. Nos. 5,340,740 issued Aug. 23, 1994 to Petitte et al.; 5,656,479 issued Aug. 12, 1997 to Petitte et al.; and 5,830,510 issued Nov. 3, 1998 to Petitte et al. Undifferentiated avian cells expressing an ESC phenotype are useful, among other things, as a tool for the study of embryological development (i.e., by labeling the cells with a marker gene and observing their distribution after injection in vivo) and the production of transgenic poultry. They are useful in allowing the application of homologous recombination to the production of transgenic poultry. In view of such uses, the development of additional methods for obtaining undifferentiated avian cells expressing an ESC phenotype represents a continuing need in the art.

SUMMARY OF THE INVENTION

A method of producing a sustained culture of undifferentiated avian cells expressing an embryonic stem cell phenotype is disclosed. A preferred embodiment of the method comprises: (a) collecting avian cells comprising primordial germ cells from an avian embryo after formation of the primitive streak; (b) depositing the avian cells in contact with a preconditioned feeder matrix; and (c) growing the avian cells on the feeder matrix in the presence of media for a time sufficient to produce an avian cell culture consisting essentially of undifferentiated avian cells expressing an embryonic stem cell phenotype.

The avian cells are collected from an embryo later than stage 14 (H&H), preferably from a stage 14 to stage 45 embryo, more preferably from a stage 15 to stage 31 embryo, and even more preferably from a stage 27 to stage 30 embryo. More preferably, the avian cells are deposited in contact with the feeder matrix in a number ranging from about 10,000 to about 20,000 cells. Even more preferably, about 20,000 avian cells are deposited in contact with the feeder matrix.

The feeder matrix may comprise fibroblast cells. The fibroblast cells can be present in the feeder matrix in a number ranging from about 40,000 to about 60,000 cells, preferably from about 50,000 to about 60,000 cells, even more preferably, from about 55,000 to about 60,000 cells. Most preferably, about 60,000 fibroblast cells are present in the feeder matrix.

Preferably, the fibroblast cells comprise mouse fibroblast cells, more preferably mouse STO fibroblast cells. In a preferred embodiment, the mouse fibroblast cells form a mouse fibroblast feeder layer.

The avian embryo is a embryo optionally selected from the group including but not limited to chicken, turkey, duck, goose, quail and pheasant embryo. In a preferred embodiment, the avian embryo is a chicken embryo.

Accordingly, it is an object of the present invention to provide a novel process for the culturing of undifferentiated avian cells expressing an embryonic stem cell phenotype.

It is another object of the present invention to provide a process for the culturing of undifferentiated avian cells expressing an embryonic stem cell phenotype from avian cells comprising primordial germ cells.

It is a further object of the present invention to provide a feeder matrix for use in preparing a culture of undifferentiated avian cells expressing an embryonic stem cell phenotype using avian primordial germ cells.

It is yet a further object of the present invention to characterize an optimal number of avian cells comprising primordial germ cells for use in establishing a culture of undifferentiated avian cells expressing an embryonic stem cell phenotype.

Some of the objects of the invention having been stated herein above, other objects will become evident as the description proceeds, when taken in connection with the accompanying Laboratory Examples and Drawings as best described herein below.

10,000 gonadal cells per well were seeded on different numbers of STO cells (50,000, 55,000 and 60,000 cells per well). Stage-specific mouse embryonic antigen-1 (SSEA-1—a marker for PGCs and ESCs)-positive cells were counted as the number of PGCs at 0, 1 and 3 days after culture. In the 60,000 cells per well group the number of PGCs show higher than the other groups at day 3 (P<0.05). This result indicates that a substantially complete monolayer of feeder cells, e.g. a monolayer comprising about 60,000 cells, is preferred for the PGCs culture.

Figure 2:
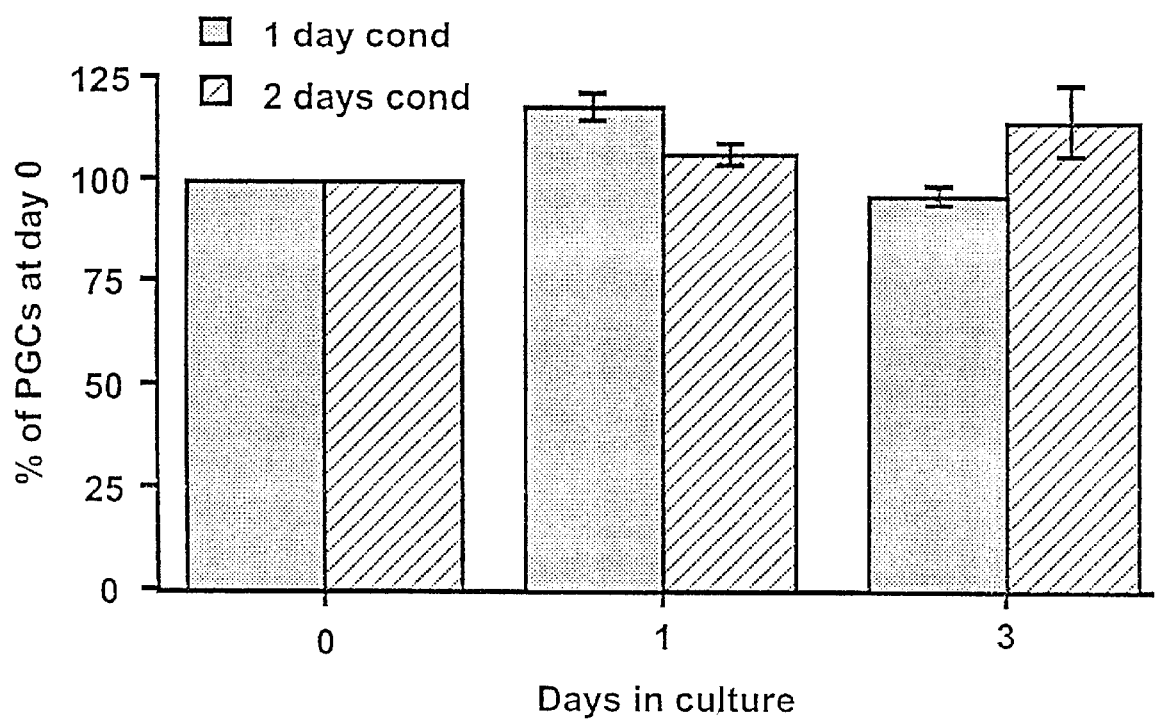

FIG. 2 is a bar graph depicting survival rate of gonadal PGC cultures using preconditioned STO feeder cells. 20,000 gonadal cells per well were seeded on 60,000 STO cells per well after 1 or 2 days preconditioning. PGCs show a high survival rate with 2 days preconditioning.

Figure 3:
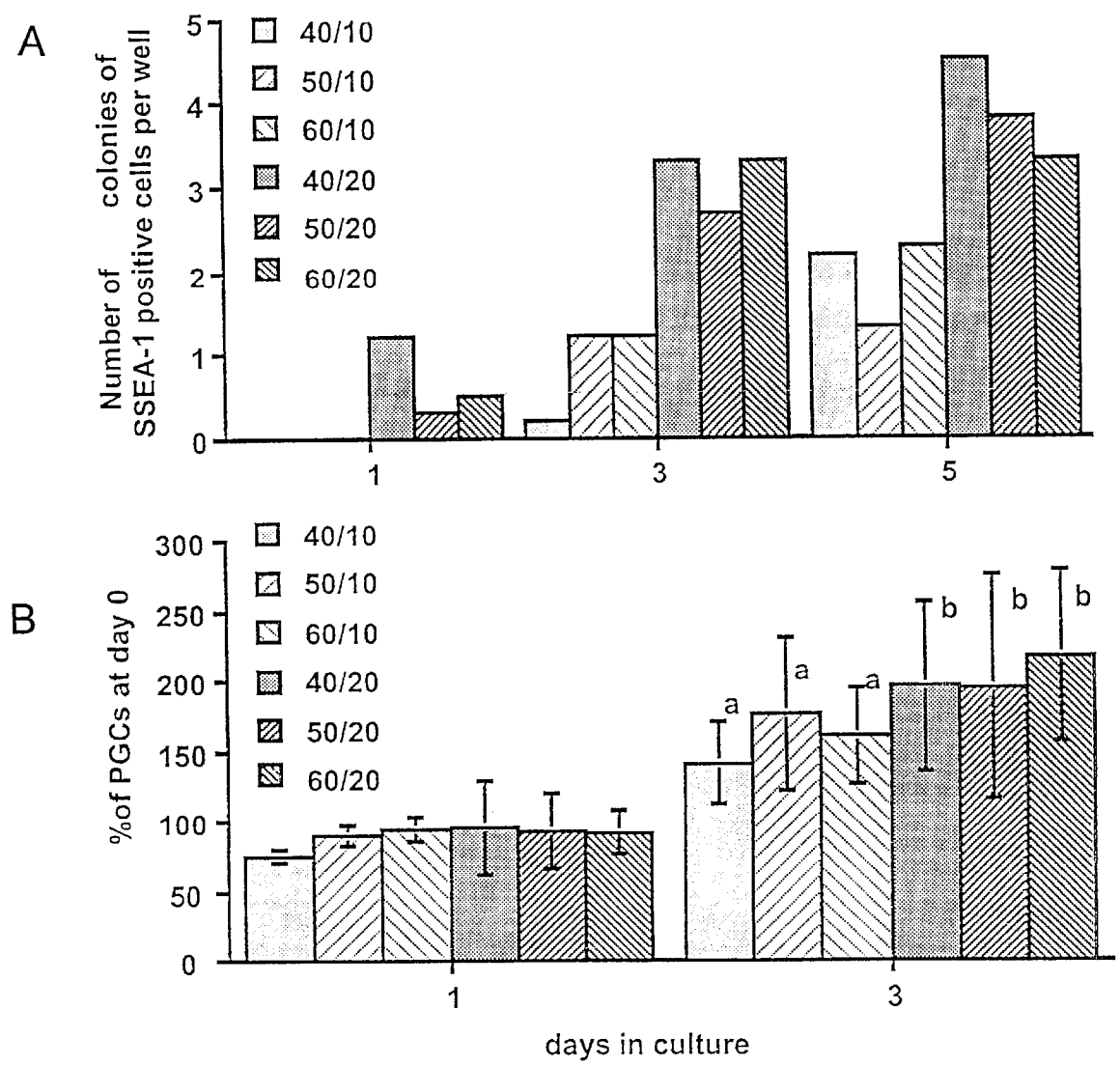

FIG. 3 is a set of bar graphs depicting the effects of seeding differing numbers of gonadal cells per culture well.

FIG. 3A is a bar graph depicting the number of colonies greater than 20 SSEA-1 positive cells on different number of STO cells (40,000, 50,000 or 60,000 per well—referred to as "40", "50", and "60" on the Legend presented on FIG. 3A) after seeding 10,000 or 20,000 gonadal cells per well (referred to as "10" and "20" on the Legend presented on FIG. 3A). Thus, on the Legend presented on FIG. 3A, the designations "40/10", "50/10" and "60/10" respectively refer to STO cells numbering 40,000, 50,000 or 60,000 per well and to the seeding of 10,000 gonadal cells per well, and the designations "40/20", "50/20" and "60/20" respectively refer to STO cells numbering 40,000, 50,000 or 60,000 per well and to the seeding of 20,000 gonadal cells per well.

FIG. 3B is a bar graph depicting proliferation of gonadal PGCs on different number of STO cells (40,000, 50,000 or 60,000 per well—referred to as "40", "50", and "60" on the Legend presented on FIG. 3B) after seeding 10,000 or 20,000 gonadal cells per well (referred to as "10" and "20" on the Legend presented on FIG. 3B). Thus, on the Legend presented on FIG. 3B, the designations "40/10", "50/10" and "60/10" respectively refer to STO cells numbering 40,000, 50,000 or 60,000 per well and to the seeding of 10,000 gonadal cells per well, and the designations "40/20", "50/20" and "60/20" respectively refer to STO cells numbering 40,000, 50,000 or 60,000 per well and to the seeding of 20,000 gonadal cells per well. The proliferation of individual PGCs was higher (P<0.05) using 20,000 gonadal cells versus 10,000 gonadal cells. Similarly, the number of SSEA-1 positive colonies formed after 5 days was dependent on the number of gonadal cells seeded.

FIG. 4 is a series of photographs showing SSEA-1 staining of chicken gonadal cells cultured on STO cells for five days, as described above for FIG. 3.

Figure 4A:
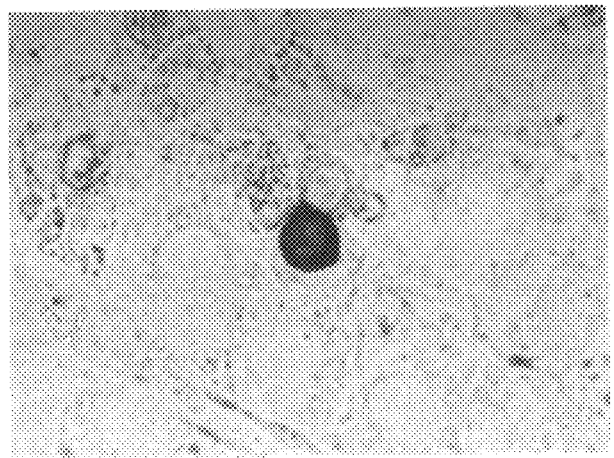

FIG. 4A depicts freshly seeded culture (day 0) showing an individual SSEA-1 positive PGC. Only PGCs were positive for the SSEA-1 epitope at the initiation of culture.

Figure 4B:
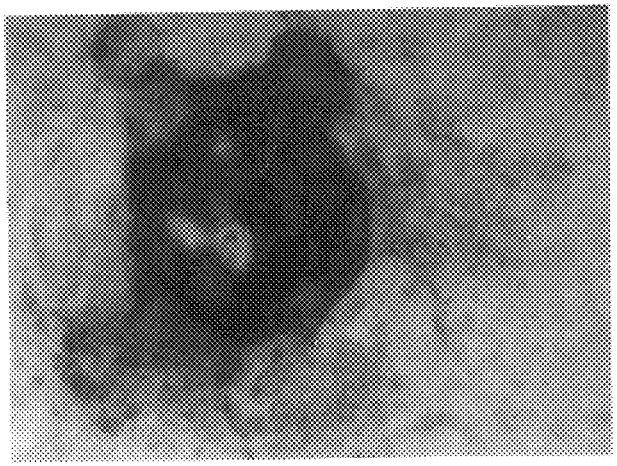

FIG. 4B depicts a colony of SSEA-1 positive ES cells after culture for three days.

Figure 4C:
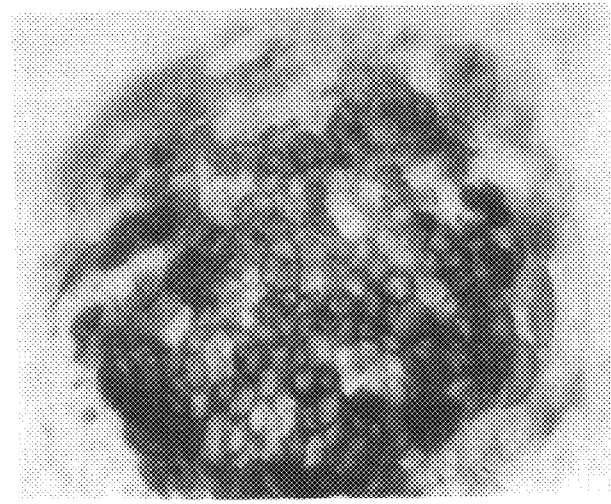

FIG. 4C depicts a large colony of PGC-derived ES cells after three days of culture.

Figure 4D:
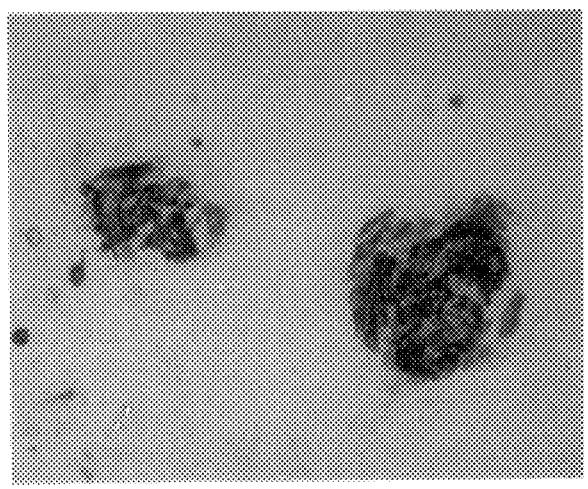

FIG. 4D depicts a low magnification image of a 3-day culture stained with SSEA-1. Note the individually stained PGCs and the colonies of SSEA-1 positive ES cells.

Figure 4E:
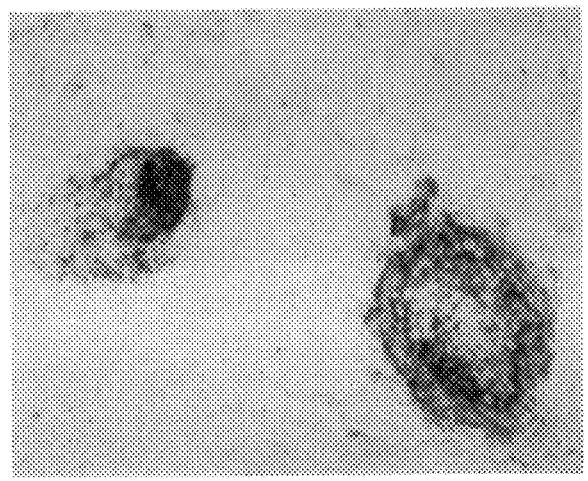

FIG. 4E depicts SSEA-1 staining of ES cell colonies after 5 days of culture.

Figure 4F:
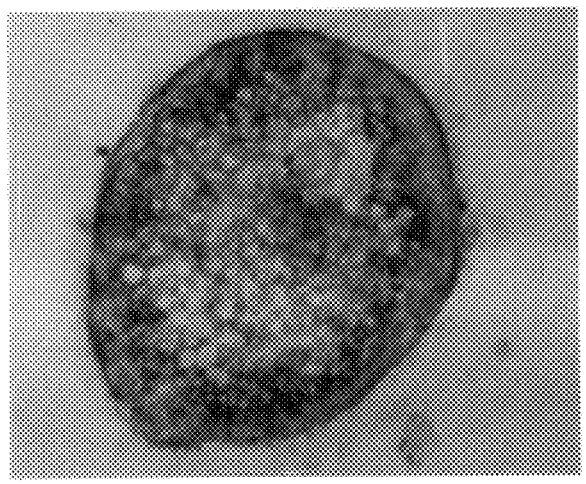

FIG. 4F depicts a high magnification image of a PGC-derived ES cell colony after 5 days of culture.

DETAILED DESCRIPTION OF THE INVENTION

In mammals, primordial germ cells cultured from the genital ridge have the ability to give rise to pluripotent embryonic stem cells. However, reports on the culture of avian PGCs have concentrated on efforts to maintain a PGC-phenotype and to stimulate proliferation. Thus, an object of the present invention was to develop and provide a process that would permit the development of undifferentiated avian cells expressing an embryonic stem cell phenotype from avian PGCs.

Unlike PGC isolates from mammalian embryos as disclosed in, for example, U.S. Pat. Nos. 5,690,926 issued Nov. 25, 1997 to Hogan, 5,670,372 issued Sep. 23, 1997 to Hogan, and 5,537,357 issued Sep. 26, 1995 to Hogan, the avian gonadal cells comprising primordial germ cells isolated in accordance with the present invention also comprise a significant number of stromal cells. The presence of the stromal cells adds a complication development of the process of the present invention that is not observed in mammalian systems.

While the following terms are believed to be well understood by one of ordinary skill in the art, the following definitions are set forth to facilitate explanation of the invention.

The term "avian" as used herein refers to any avian species, including but not limited to Gallinacea sp., chicken, turkey, duck, goose, quail and pheasant. Chicken is currently preferred.

The term "sustained" as used herein with respect to ES cells and ES cell cultures refers to a cell or cell culture capable of undergoing further cell division, even if the cells are eventually subject to senescence.

The phrase "embryonic stem cell phenotype" refers to undifferentiated avian cells having a large nucleus, a prominent nucleolus, and little cytoplasm.

It has been reported that mouse PGCs maintained on STO feeder cell monolayers in the presence of LIF and bFGF resulted in cells resembling embryonic stem cells. See Resnick et al. *Nature* 359:550–551 (1992); Matsui et al., *Cell* 70:841–843 (1992). Resnick et al. *Nature* 359:550–551 (1992) suggested that such cells be designated "embryonic germ" (EG) for convenience cells to imply that they originated from PGCs in vitro. However, it is recognized among those of ordinary skill in the art that embryonic germ cells and embryonic stem cells are phenotypically the same in that they appear to be the same upon microscopic inspection (despite reported differences in methylation of some genes), display the same immunological markers, and are functionally the same in that both have been shown to differentiate extensively in culture and to contribute to chimeras when injected into host blastocysts, thus demonstrating their pluripotent and totipotent nature. Accordingly, the phrase "undifferentiated avian cell expressing an embryonic stem cell phenotype" encompasses cells derived from avian primordial germ cells and is therefore used to describe the cells cultured in accordance with the process of the present invention.

Following long-standing patent law convention, the terms "a" and "an" mean "one or more" when used in this application, including the claims.

Avian embryos from which cells are obtained for carrying out the present invention are preferably in a stage after the formation of the primitive streak and are preferably in a stage prior to sexual differentiation. Avian embryos from which cells are obtained for carrying out the present invention are preferably after stage 14, more preferably stage 14 to stage 45, even more preferably stage 15 to stage 31, including stages 17, 18, 19, 20 and 21, and most preferably in stage 27 to 30 of development on the Hanburger & Hamilton (H&H) staging system.

Such embryos may conveniently be obtained from fertilized eggs that were incubated for about 55 to about 168 hours (i.e. about 2 to about 7 days), more preferably for about 72 to about 168 hours (i.e. about 3 to 7 days), even more preferably for about 96 to about 168 hours (i.e. about 4 to 7 days), and even more preferably for about 96 to about 120 hours (i.e. about 4 to 5 days). In a preferred embodiment embryonic gonadal PGCs and stromal cells may be collected from the embryonic gonads using a suitable solution, such as EDTA and/or a buffering solution. Preferably, care is taken to obtain a single cell suspension.

Thus, an aspect of the present invention pertains to the production of undifferentiated avian cells expressing an embryonic stem cell phenotype from avian gonadal cells comprising primordial germ cells collected from an avian embryo. Prior to the disclosure of the present invention, it was the general view among those of ordinary skill in the art that avian embryonic gonadal cells comprising primordial germ cells, such as may be collected from, for example, the avian embryonic genital ridge or gonad, once the embryo had reached a stage associated with gonadal development, were to terminally differentiate to germ cells only. The present invention shows that a portion of avian gonadal cells comprising primordial germ cells collected from, for example, the genital ridge or gonads, of an avian embryo become undifferentiated cells expressing an embryonic stem cell phenotype. Hence, the process of the present invention provides for convenience during the culturing of undifferentiated cells expressing an embryonic stem cell phenotype in that the primordial germ cells may be isolated in greater numbers from, for example, the genital ridge or gonads, and are typically easier to isolate in view of the more advanced development of the avian embryo.

Typically, the cultures of the present invention include a feeder matrix as defined herein. A feeder matrix can either be cells or cell lines cultured for the purpose of obtaining ESCs. Alternatively, a feeder matrix can be derived from or provided by the organ or tissue in which the primordial germ cells are located, e.g., the gonad. Alternatively, the feeder cells comprising the feeder matrix could be substituted with extracellular matrix plus bound growth factors.

A feeder matrix as used herein is constructed in accordance with procedures known in the art. As noted above, it is preferred that the feeder matrix be preconditioned. By the term "preconditioned" it is meant that the feeder matrix is cultured in the presence of media for a period of time prior to the depositing of gonadal cells comprising primordial germ cells in contact with the feeder matrix, e.g. a time sufficient to initiate and establish production of, for example, growth factors or other factors by the feeder matrix. As disclosed in the Laboratory Examples, a feeder matrix is preconditioned by culturing the feeder matrix by itself for one to two days prior to the depositing of gonadal cells comprising primordial germ cells in contact with the feeder matrix.

The feeder matrix preferably comprises mouse fibroblast cells. STO fibroblasts are preferred, but primary fibroblasts are also suitable. Also, while the present invention has been described with respect to the use of mouse cell feeder matrices, it is contemplated that feeder matrices comprising cells from other murine species (e.g., rat); other mammalian species (e.g., ungulate, bovine, and porcine species); or avian species (e.g. Gallinacea, chicken, turkey, duck, goose, quail and pheasant) may also be used.

The culturing process of the present invention may optionally comprise establishing a monolayer of feeder cells. Feeder cells may mitotically inactivated using standard techniques. For example, the feeder cells may be exposed to gamma radiation (e.g. 4000 Rads of gamma radiation) or may be treated with Mitomycin C (e.g. 10 $\mu$g/ml for 2–3 hours). Procedures for mitotically inactivating cells are also detailed in the information typically sent with cells from the American Type Culture Collection (ATCC), 10801 University Boulevard, Manassas, Va. 20110-2209 (e.g. STO feeder cells are available under ATCC accession number 1503). Monolayers may optionally be cultured to about 80% confluency, preferably to about 90% confluency, and more preferably about 100% confluency. While configuration of the feeder cells as a monolayer is the preferred configuration for the culture, any suitable configuration is contemplated to be within the scope of the present invention. Thus, for example, layers, monolayers, clusters, aggregates or other associations or groupings of feeder cells are contemplated to fall within the scope of the present invention and are particularly contemplated to fall with the meaning of the term "matrix".

Thus, the avian PGCs can extend non-uniformly through the feeder cells vertically, horizontally, diagonally, or in any combination thereof, such that cell aggregates are formed. In accordance with the present invention, it is thus contemplated that the cultures can be formed by mixing PGCs with appropriate feeder cells and inserting the mixture into a suitable culture container, such as a multi-well plate.

The media used in carrying out the present invention may be any suitable media. The media may be a conditioned media or a synthetic media, both of which are known in the art. Conditioned media, and particularly BRL conditioned media, is currently preferred. By way of example, BRL conditioned media is prepared according to art-recognized techniques, such as described by Smith. A. G. and Hooper, M. L., Dev. Biol. 1987 May; 121(1): 1–9. BRL cells are available from ATCC under accession number CRL-1442. Optionally, the media may be supplemented with growth factors, including but not limited to leukemia inhibitory factor (LIF), insulin-like growth factor (IGF), fibroblast growth factor (FGF), basic fibroblast growth factor (bFGF), stem cell factor (SCF—also called steel factor or SF), transforming growth factor-$\beta$1 (TGF-$\beta$1) and anti-retinoic acid.

In a preferred embodiment, avian embryonic gonadal cells comprising primordial germ cells from a four to five day incubated avian embryo are seeded onto the preconditioned feeder matrix with conditioned media, and the avian cells give rise to nests or colonies of cells exhibiting an embryonic stem cell phenotype. Unlike the case with mammalian stem cells, it is currently preferred to have a preconditioned feeder matrix to facilitate the survival and development of avian PGCs into undifferentiated avian cells expressing an ESC phenotype. The avian embryo cells of the present invention can be cultured for at least one or two months as is typical for a primary cell culture, which is significantly greater than the usual two week life of primary cultures of cells from an unincubated avian embryo.

Cell cultures of the present invention may be formulated for administration to animals by dissociating the cells (e.g., by mechanical dissociation) and intimately admixing the cells with a pharmaceutically acceptable carrier (e.g., phosphate-buffered saline (PBS) solution). Avian cells in such formulations may be prepared to carry a heterologous DNA sequence into an avian subject in the manner described in greater detail below.

The undifferentiated avian cells produced by the process of the present invention are useful, among other things, as a tool for the study of embryological development (i.e., by labeling the cells with a marker gene and observing their distribution after injection in vivo) and the production of transgenic poultry. They are useful in allowing the application of homologous recombination to the production of transgenic poultry.

The undifferentiated avian cells expressing an embryonic stem cell phenotype should also be useful for the production of chimeric avians, including transgenic chimeric avians. It is contemplated that transgenic chimeric avians will be useful for the recovery of heterologous proteins, which preferably can be recovered directly of the eggs of such chimeric transgenic avians. For example, such avians can be used for the production and recovery of therapeutic proteins and other polypeptides.

In avian species, certain donor cell types have been isolated that retain viability when injected into recipient embryos. See Etches et al., *Poultry Science* 72:882–887 (1993); Etches et al., in *Avian Incubation*, Chapter 22, Butterworth Publishers (1990); Verrinder Gibbins et al., *Fourth World Congress on Genetics Applied to Livestock Production*, Edinburgh, (1990); Petitte et al., *Development* 108, 185–189 (1990)). These studies showed that blastodermal cells derived from Stage X embryos (embryo at oviposition) remained viable when transferred to comparable recipient Stage X embryos. Thus, the present invention provides a new method of altering the phenotype of a bird and the birds so produced with the avian embryonic stem cells disclosed herein. The method comprises transfecting avian embryonic stem cells as disclosed herein with the DNA sequence in vitro (e.g., by electroporation or transformation with a retroviral vector), and then injecting the transfected embryonic stem cells into an egg containing an embryonic bird (e.g., into the yolk sac or onto the chorioallantoic membrane, preferably into the subgerminal cavity, and preferably during early embryonic development (e.g., prior to day 2 or 3 of incubation, and most preferably prior to day 1 of incubation)), with the DNA sequence being effective to cause a change in phenotype in the bird after hatch (e.g., a change in protein expression, a change in growth rate, feed efficiency, disease resistance, or a combination of all of these factors).

Preferably, the egg into which the DNA is introduced is incubated to hatch, and the bird so produced is raised to at least an age at which the change in phenotype is expressed. It is of no deleterious consequence if the transformed embryo and bird is chimeric, so long as a physiological response is achieved in the animal after hatch sufficient to evoke a measurable phenotypic change measured in any suitable way. By way of additional example, protein expression in the chimera, or transgenic offspring thereof produced by germ line transmission of the DNA sequence, may be established through incorporation of an inducible promoter into the introduced DNA sequence coupled with treatment of the chimera, or transgenic offspring thereof, with an agent which induces the promoter.

The mechanism of in ovo injection is not critical, but it is preferred that the method not unduly damage the tissues and organs of the embryo or the extraembryonic membranes surrounding it so that the treatment will not decrease hatch rate. For example, applicants have carried out in ovo injections by forming a window in an egg and then using a micro-pipette or needle for the injection, such a 50 $\mu$m-diameter micro-pipette or a 50 $\mu$m-diameter needle. If desired, the egg can be sealed with a substantially bacteria-impermeable sealing material such as wax or the like to prevent subsequent entry of undesirable bacteria. Suitable sealing material may optionally comprise biologically acceptable antimicrobial compositions.

It is envisioned that a high speed automated injection system for avian embryos will be particularly suitable for practicing the present invention. All such devices, as adapted for practicing the present invention, comprise an injector containing the undifferentiated avian cell expressing an embryonic stem cell phenotype as described herein, with the injector positioned to inject an egg carried by the apparatus with the DNA. In addition, a sealing apparatus operatively associated with the injection apparatus may be provided for sealing the hole in the egg after injection thereof.

The DNA sequence introduced in ovo with embryonic stem cells of the invention is, in general, a construct comprised of a promoter functional in avian cells and a gene encoding a peptide or protein operably linked to the promoter. Preferably, the protein or peptide is physiologically active and capable of producing a phenotypic change in the bird. In general, the DNA construct may be a linear DNA sequence (introduced into the embryonic stem cells of the invention by electroporation) or a sequence carried by a vector or other suitable carrier for transforming the embryonic stem cells of the invention using various techniques known in the art, such as liposomes, calcium phosphate, electroporation, or DMSO. Vectors, as discussed below, may be plasmids, viruses (including retroviruses), and phage, whether in native form or derivatives thereof.

Illustrative of genes encoding a protein or peptide are those which encode a protein or peptide selected from the group consisting of growth hormone, thyroid releasing hormone (TRH), Marek's MDX, and immunogenic recombinant antigens such as that for coccidiosis.

The production of cloned genes, recombinant DNA, vectors, transformed host cells, proteins and protein fragments by genetic engineering is well known. See e.g., U.S. Pat. Nos. 4,761,371 to Bell et al. at Col. 6 line 3 to Col. 9 line 65; 4,877,729 to Clark et al. at Col. 4 line 38 to Col. 7 line 6; 4,912,038 to Schilling at Col. 3 line 26 to Col. 14 line 12. Protocols for restriction endonuclease digestion, preparation of vectors, DNA purification and other such procedures are essentially as described in standard cloning manuals. See Sambrook et al., *Molecular Cloning, a Laboratory Manual*, (2d Ed., Cold Spring Harbor Press, N.Y. (1989)).

A vector is a replicable DNA construct used herein to either amplify and/or express DNA encoding the gene of interest. A suitable expression vector will have controlling elements capable of expressing the cloned cDNA or genomic DNA placed in the correct orientation when the vector is introduced into the correct host. Such elements typically include but are not limited to a promoter region which interacts specifically with cellular proteins involved in transcription or which may be inducible by administration of an inducing agent, enhancer elements which can stimulate transcription many-fold from linked heterologous promoters, a splice acceptor and/or donor sequence, and termination and polyadenylation signals. Also required is the sequence for a ribosome binding site capable of permitting translation and which is operably linked to the gene to be expressed. Recently, a muscle-specific promoter has been isolated which is positioned upstream of both the skeletal muscle structural gene and the essential proximal promoter element and is operably associated with each. (Mar and Ordahl, *Proc. Natl. Acad. Sci. USA* 85, 6404–6408 (1988)). Vectors comprise plasmids, viruses (e.g. adenovirus, cytomegalovirus), phage, and DNA fragments integratable into the host genome by recombination. The vector may optionally replicate and function independently of the host genome, or may in some instances integrate into the genome itself.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Example 1

Collection of Gonadal Cells

A mixture of gonadal PGCs and stromal cells were collected from stage 27–30 (H&H) embryonic gonads using EDTA. Care was taken to obtain a single cell suspension. Particularly, the gonads from stage 27–30 (H&H) chicken embryos were collected by blunt dissection and pooled in a drop of $Ca^{2+}$- and $Mg^{2+}$-free phosphate buffered saline (PBS(-)). After collection from the embryos, the gonads were put into one ml of 0.02% EDTA in a 1.5 ml Eppendorf tube and then put in a 37° C. incubator for 10 minutes. The tube was then centrifuged at 200 G for 3 minutes and the supernatant was removed. The collected gonads were then passed through a cell strainer (FALCON® 2360, 100 µM pore size) with DMEM containing 10% of fetal bovine serum (FBS) to a new tube. This provided a single cell suspension.

Irradiated STO feeder layers were prepared in 96 well plates using DMEM containing 10% FBS. Several culture parameters were then tested, including source of FBS, number of feeder cells, batch of STO cells (old vs. new), preconditioning of the feeder layer, and the number of gonadal cells seeded.

Example 2

Culturing of Gonadal Cells

Gonadal cells were cultured on STO feeder layers for 3–5 days and stained with anti-SSEA-1. The number of single SSEA-1 positive PGCs and the number of SSEA-1 positive colonies were examined at day 0, 1, 3 and 5 of culture. In most cases, there was considerable PGC death in the first 24 hours of culture followed by an increase in the number of single PGCs on days 3–5. The survival and proliferation of the gonadal PGCs was affected by the quality of the STO feeder layer, the number of STO cells seeded, preconditioning of the STO feeder layer, and the number of gonadal cells initially seeded. Considerable variation between experiments was observed within one batch of FBS, suggesting that the source of FBS may influence the culture.

Figure 1:
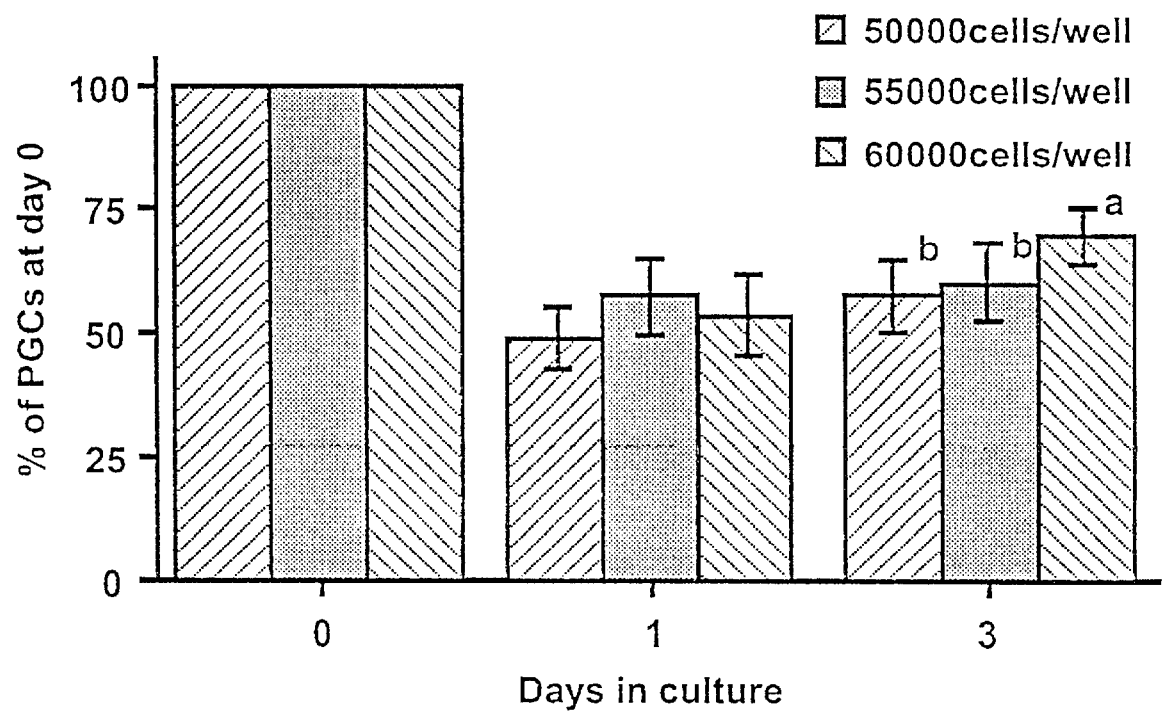
FIG. 1 is a bar graph depicting the survival rate of gonadal PGCs on different number of STO feeder cells in culture.

FIG. 1 shows the survival rate of gonadal PGCs on different numbers of STO feeder cells in culture. 10,000 cells per well of gonadal cells were seeded on different numbers of STO cells: 50,000, 55,000 and 60,000 cells per well. The SSEA-1 positive cells were counted as the number of PGCs at 0, 1 and 3 days after culture. In the 60,000 cells per well group the number of PGCs are higher than the other groups at day 3 ($P<0.05$). This result indicates that the complete monolayer of feeder cells is preferred for PGC culture.

Example 3

Preconditioning of the STO Feeder Layer

Preconditioning of the STO feeder layer ameliorated the initial cell death seen within the first 24 hours. By 3 days of culture, colonies of SSEA-1 positive cells could be found along with single PGCs. These colonies increased in number and size after five days of culture. The cells within the colonies were smaller than PGCs and tightly packed with well-defined colony borders and thus expressed an embryonic stem cell phenotype. Some colonies were estimated to contain more than 2,000 cells. The mixture of PGCs and ESC-like colonies suggests that only a fraction of the gonadal PGCs could develop an ESC phenotype.

FIG. 2 shows the survival rate of gonadal PGC cultures using preconditioned STO feeder cells. 20,000 gonadal cells per well were seeded on 60,000 STO cells per well after 1 or 2 days preconditioning. PGCs show a high survival rate with 2 days preconditioning.

Example 4

Dosages of Gonadal Cells

FIG. 3A shows the number of colonies greater than 20 SSEA-1 positive cells on different numbers of STO cells (40,000, 50,000 or 60,000 per well) after seeding 10,000 or 20,000 gonadal cells per well. The number of colonies having greater than 20 SSEA-1 positive cells was determined to differentiate colonies comprising undifferentiated cells expressing an ESC phenotype from individual PGCs and random groupings of PGCs in a conservative manner.

FIG. 3B shows proliferation of gonadal PGCs on different number of STO cells (40,000, 50,000 or 60,000 per well) after seeding 10,000 or 20,000 gonadal cells per well. The proliferation of individual PGCs was higher ($P<0.05$) using 20,000 gonadal cells versus 10,000. Similarly, the number of SSEA-1 positive colonies formed after 5 days was dependent on the number of gonadal cells seeded.

REFERENCES

The references listed below as well as all references cited in the specification are incorporated herein by reference to the extent that they supplement, explain, provide a background for or teach methodology, techniques and/or compositions employed herein.

Allioli, N. et al., *Dev. Biol.* 1994 September; 165(1): 30–7.

Chang, I. K. et al., *Cell. Biol. Int.* 1995 February; 19(2): 143–9.

Chang. I. K. et al., *Cell. Biol. Int.* 1997 August; 21(8): 495–9.

Etches et al., in *Avian Incubation*, Chapter 22, Butterworth Publishers (1990).

Etches et al., *Poultry Science* 72:882–887 (1993).

Mar and Ordahl, *Proc. Natl. Acad. Sci. USA* 85, 6404–6408 (1988).

PCT Publication No. WO 96/12793, published May 2, 1996.

PCT Publication No. WO 99/06533, published Feb. 11, 1999.

PCT Publication No. WO 99/06534, published Feb. 11, 1999.

Petitte et al., *Development* 108, 185–189 (1990).

Smith, A. G. and Hooper, M. L., *Dev. Biol.* 1987 May; 121(1): 1–9.

U.S. Pat. Nos. 4,040,388, 4,469,047, 4,593,646, 4,681,063, 4,761,371, 4,877,729, 4,903,625, 4,912,038, 5,340,740, 5,537,357, 5,656,479, 5,670,372, 5,690,926, 5,830,510.

Sambrook et al., *Molecular Cloning, a Laboratory Manual*, (2d Ed., Cold Spring Harbor Press, N.Y. (1989).

Verrinder Gibbins et al., *Fourth World Congress on Genetics Applied to Livestock Production*, Edinburgh, (1990).

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of producing a sustained culture of undifferentiated avian cells expressing an embryonic stem cell phenotype, comprising:
    (a) collecting avian gonadal cells comprising primordial germ cells from an avian embryo after formation of the primitive streak;
    (b) depositing the avian gonadal cells in contact with a preconditioned feeder matrix; and
    (c) growing the avian gonadal cells on the preconditioned feeder matrix in the presence of media for a time sufficient to produce an avian cell culture consisting essentially of undifferentiated avian cells expressing an embryonic stem cell phenotype.

2. The method of claim 1, wherein the avian gonadal cells are collected from a stage 14 to stage 45 embryo.

3. The method of claim 2, wherein the avian gonadal cells are collected from a stage 15 to stage 31 embryo.

4. The method of claim 3, wherein the avian gonadal cells are collected from a stage 27 to stage 30 embryo.

5. The method of claim 1, wherein the avian gonadal cells are deposited in contact with the preconditioned feeder matrix in a number ranging from about 10,000 to about 20,000 cells.

6. The method of claim 5, wherein about 20,000 avian gonadal cells are deposited in contact with the preconditioned feeder matrix.

7. The method of claim 1, wherein the preconditioned feeder matrix comprises fibroblast cells.

8. The method of claim 7, wherein fibroblast cells are present in the preconditioned feeder matrix in a number ranging from about 40,000 to about 60,000 cells.

9. The method of claim 8, wherein fibroblast cells are present in the preconditioned feeder matrix in a number ranging from about 50,000 to about 60,000 cells.

10. The method of claim 9, wherein fibroblast cells are present in the preconditioned feeder matrix in a number ranging from about 55,000 to about 60,000 cells.

11. The method of claim 10, wherein about 60,000 fibroblast cells are present in the preconditioned feeder matrix.

12. The method of claim 7, wherein the fibroblast cells are mouse fibroblast cells.

13. The method of claim 12, wherein mouse fibroblast cells form a mouse fibroblast feeder layer.

14. The method of claim 12, wherein the mouse fibroblast cells are mouse STO fibroblast cells.

15. The method of claim 1, wherein the undifferentiated avian cells are capable of maintaining the stem cell phenotype when grown on the preconditioned fibroblast feeder matrix in the presence of the media for at least three days.

16. The method of claim 1, wherein the avian embryo is a embryo selected from the group consisting of chicken, turkey, duck, goose, quail and pheasant embryo.

17. The method of claim 15, wherein the avian embryo is a chicken embryo.

18. The method of claim 1, wherein the media is a conditioned media.

19. A method of producing a sustained culture of undifferentiated avian cells expressing an embryonic stem cell phenotype, comprising:
    (a) collecting avian gonadal cells comprising primordial germ cells from an avian embryo after formation of the primitive streak;
    (b) depositing the avian gonadal cells in contact with a preconditioned fibroblast feeder cell matrix; and
    (c) growing the avian gonadal cells on the feeder cell matrix in the presence of media for a time sufficient to produce an avian cell culture consisting essentially of undifferentiated avian cells expressing an embryonic stem cell phenotype.

20. The method of claim 19, wherein the avian gonadal cells are collected from a stage 14 to stage 45 embryo.

21. The method of claim 20, wherein the avian gonadal cells are collected from a stage 15 to stage 31 embryo.

22. The method of claim 21, wherein the avian gonadal cells are collected from a stage 27 to stage 30 embryo.

23. The method of claim 19, wherein the avian gonadal cells are deposited in contact with the feeder cell matrix in a number ranging from about 10,000 to about 20,000 gonadal cells.

24. The method of claim 23, wherein about 20,000 avian gonadal cells are deposited in contact with the feeder cell matrix.

25. The method of claim 19, wherein fibroblast cells are present in the fibroblast feeder matrix in a number ranging from about 40,000 to about 60,000 cells.

26. The method of claim 25, wherein fibroblast cells are present in the fibroblast feeder matrix in a number ranging from about 50,000 to about 60,000 cells.

27. The method of claim 26, wherein fibroblast cells are present in the fibroblast feeder matrix in a number ranging from about 55,000 to about 60,000 cells.

28. The method of claim 27, wherein about 60,000 fibroblast cells are present in the fibroblast feeder matrix.

29. The method of claim 19, wherein the fibroblast feeder matrix comprises mouse fibroblast cells.

30. The method of claim 29, wherein the mouse fibroblast cells are mouse STO fibroblast cells.

31. The method of claim 19, wherein the undifferentiated avian cells are capable of maintaining the stem cell phenotype when grown on the fibroblast feeder matrix in the presence of the media for at least three days.

32. The method of claim 19, wherein the avian embryo is a embryo selected from the group consisting of chicken, turkey, duck, goose, quail and pheasant embryo.

33. The method of claim 32, wherein the avian embryo is a chicken embryo.

34. The method of claim 19, wherein the media is a conditioned media.

35. A method of producing a sustained culture of undifferentiated chicken cells expressing an embryonic stem cell phenotype, comprising:
    (a) collecting gonadal cells from a stage 27 to stage 30 chicken embryo;
    (b) depositing the gonadal cells in contact with a preconditioned mouse fibroblast feeder cell layer;

(c) growing the gonadal cells on the preconditioned mouse fibroblast feeder cell layer in the presence of a conditioned media for a time sufficient to produce a sustained avian cell culture, the sustained avian cell culture consisting essentially of undifferentiated avian cells expressing an embryonic stem cell phenotype.

36. The method of claim 35, wherein the gonadal cells are deposited in contact with the preconditioned mouse feeder cell layer in a number ranging from about 10,000 to about 20,000 gonadal cells.

37. The method of claim 36, wherein about 20,000 gonadal cells are deposited in contact with the preconditioned mouse feeder cell layer.

38. The method of claim 35, wherein fibroblast cells are present in the preconditioned mouse fibroblast feeder layer in a number ranging from about 40,000 to about 60,000 cells.

39. The method of claim 38, wherein fibroblast cells are present in the preconditioned mouse fibroblast feeder layer in a number ranging from about 50,000 to about 60,000 cells.

40. The method of claim 39, wherein fibroblast cells are present in the preconditioned mouse fibroblast feeder layer in a number ranging from about 55,000 to about 60,000 cells.

41. The method of claim 40, wherein about 60,000 fibroblast cells are present in the preconditioned mouse fibroblast feeder layer.

42. The method of claim 35, wherein the preconditioned mouse fibroblast feeder cell layer is a mouse STO fibroblast feeder cell layer.

43. The method of claim 35, wherein the undifferentiated avian cells are capable of maintaining the stem cell phenotype when grown on the preconditioned mouse fibroblast feeder layer in the presence of the media for at least three days.

* * * * *